United States Patent
Müller et al.

(10) Patent No.: US 8,663,997 B2
(45) Date of Patent: Mar. 4, 2014

(54) DEVICE AND METHOD FOR DETECTING TRACE GASES CHARACTERIZED A MECHANISM WHICH EXHALES A FILM OF FLUID TO TRAP SAID GASSES

(75) Inventors: Gerhard Müller, Grafing (DE); Andreas Helwig, Munich (DE)

(73) Assignee: EADS Deutschland GmbH, Ottobrunn (DE)

( * ) Notice: Subject to any disclaimer, the term of this patent is extended or adjusted under 35 U.S.C. 154(b) by 514 days.

(21) Appl. No.: 12/994,420

(22) PCT Filed: May 13, 2009

(86) PCT No.: PCT/EP2009/003414
§ 371 (c)(1),
(2), (4) Date: Nov. 23, 2010

(87) PCT Pub. No.: WO2009/141087
PCT Pub. Date: Nov. 26, 2009

(65) Prior Publication Data
US 2011/0071037 A1    Mar. 24, 2011

(30) Foreign Application Priority Data
May 23, 2008   (DE) .......................... 10 2008 024 769

(51) Int. Cl.
*G01N 27/00*    (2006.01)
(52) U.S. Cl.
USPC ................... 436/149; 436/181; 42/88; 42/98
(58) Field of Classification Search
USPC ........... 436/181, 149, 174, 182, 38, 100, 103, 436/106, 116, 117, 118, 119, 120, 121, 122, 436/127, 133, 134, 135, 139, 140; 422/83, 422/88, 62, 90, 91, 92, 94, 95, 96, 97, 98; 73/863
See application file for complete search history.

(56) References Cited

U.S. PATENT DOCUMENTS

| 3,370,175 A | 2/1968 | Jordon et al. |
|---|---|---|
| 5,521,101 A | 5/1996 | Saini |

(Continued)

FOREIGN PATENT DOCUMENTS

| CH | 479 868 | 1/1996 |
|---|---|---|
| DE | 44 44 607 | 5/1996 |

(Continued)

OTHER PUBLICATIONS

English Translation of International Search Report for PCT Pat. App. No. PCT/EP2009/003414, mailed Sep. 30, 2009.

(Continued)

*Primary Examiner* — Christopher A Hixson
(74) *Attorney, Agent, or Firm* — McDonnell Boehnen Hulbert & Berghoff LLP

(57) ABSTRACT

The invention relates to a gas detection system (1) for detecting gases, vapors and biological pathogens, having at least one receptor (4) arranged on a line (5) connecting the ambient air (7) to an air storage unit, wherein the gas detection system (1) is designed as a "breathing" system containing clean $CO_2$-carrying and moisture-saturated air in the air storage unit (2), wherein the operating temperature of the gas detection system (1) is the room temperature. Additionally, a method is proposed for detecting gases, vapors and biological pathogens using the inventive gas detection system. This avoids the shortcomings of the known solutions of the prior art, and an improved and more cost-effective solution for detecting trace gases is made available.

11 Claims, 3 Drawing Sheets

(56) References Cited

U.S. PATENT DOCUMENTS

Figure 1:
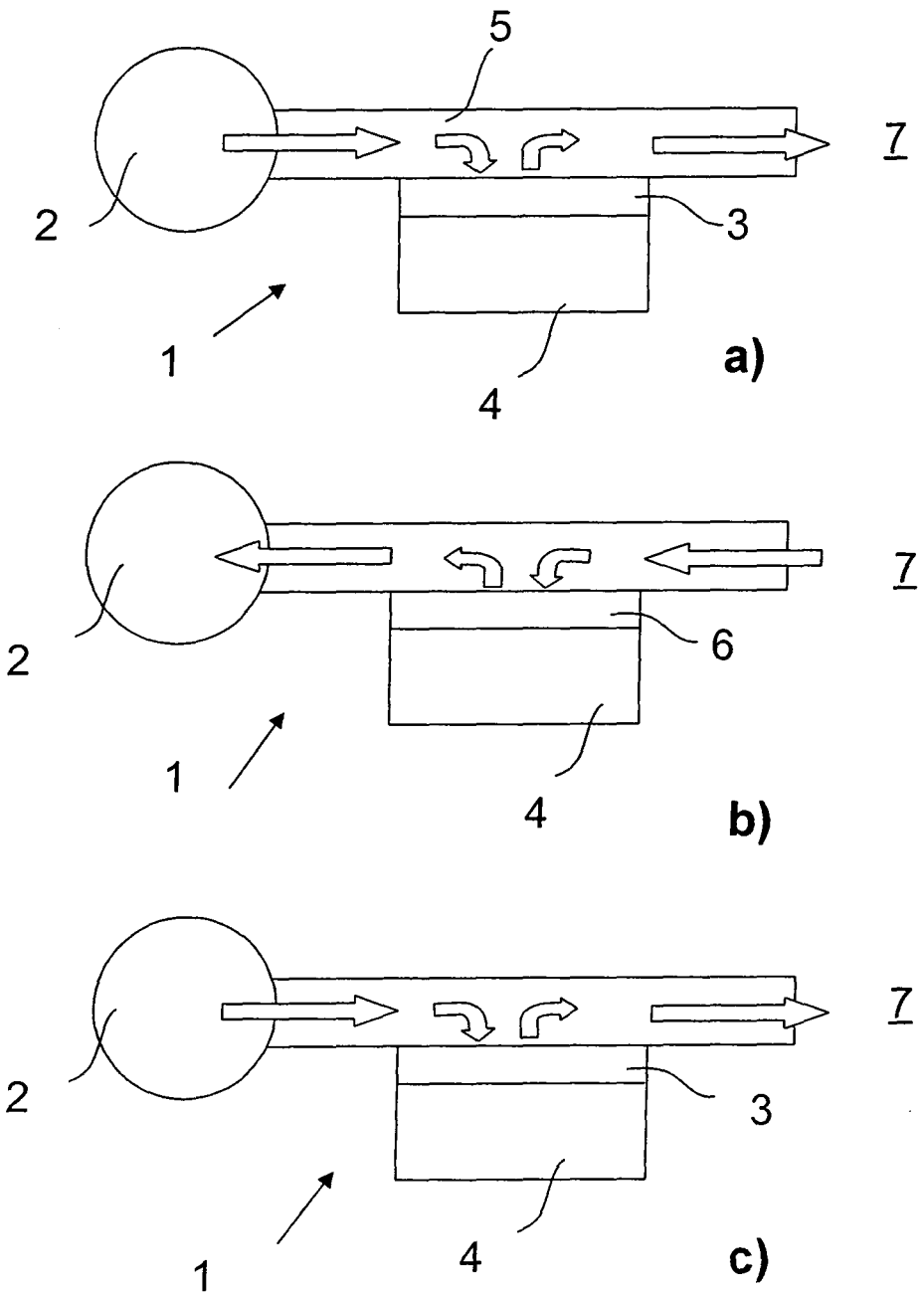

| | | |
|---|---|---|
| 6,087,183 A * | 7/2000 | Zaromb ................ 436/178 |
| 6,432,721 B1 | 8/2002 | Zook et al. |
| 6,584,827 B2 | 7/2003 | Kiesele |
| 2007/0151319 A1 | 7/2007 | Wohltjen |

FOREIGN PATENT DOCUMENTS

| | | |
|---|---|---|
| DE | 693 27 277 | 4/2000 |
| DE | 101 44 862 | 6/2006 |
| EP | 1 480 035 | 11/2004 |
| EP | 1480035 A2 | 11/2004 |
| WO | 99/01761 | 1/1999 |
| WO | 00/28318 | 5/2000 |
| WO | WO 0028318 A2 * | 5/2000 |

OTHER PUBLICATIONS

English Translation of Preliminary Report on Patentability and Written Opinion of the International Searching Authority for PCT Pat. App. No. PCT/EP2009/003414, issued Dec. 6, 2010.

* cited by examiner

DEVICE AND METHOD FOR DETECTING TRACE GASES CHARACTERIZED A MECHANISM WHICH EXHALES A FILM OF FLUID TO TRAP SAID GASSES

This is a National Stage of International Application No. PCT/EP09/003,414, filed May 13, 2009, which claims priority to DE application No. 102008024769.3, filed on May 23, 2008, both of which are incorporated herein by reference in their entirety.

The invention relates to a device for the detection of trace gases according to the preamble clause of Patent Claim 1 and a method according to Patent Claim 8.

Different sensors and sensor systems may be applied in the detection of gases and vapours. Known gas sensors are working either in diffusion-limited operation or are constantly flooded with air. Heated semiconductor gas sensors such as metal oxides, gas-sensitive field effect transistors, etc. as well as sensors depending on thermal detection principles such as recalescence and thermal conductance are widely used. Arrays comprising several sensors with different cross-sensitivities or using temperature modulation methods are often applied to overcome the limited selectivity of such sensors.

The transport of the gases to be detected to the sensitive surfaces is generally by gas diffusion. Due to the associated transport delays and also the kinetics of the adsorption and desorption processes at the sensitive surfaces, the response and decay times of the sensor signal are normally quite slow. The response time is clearly faster if the same sensor is actively flooded with the gas to be detected.

It should be noted in connection with the spectrum of potentially detected gases that all the aforementioned high temperature gas sensors have a wide spectrum of cross-sensitivity. Metal oxide sensors, for instance, basically react to all types of flammable gases (hydrocarbons, $H_2$, CO) as well as to strongly oxidising gases ($O_3$, $NO_2$, $SO_2$).

Whilst known high temperature sensors detect all gases with high sensitivity, sensors operating at low temperatures, i.e. <200° C., detect only gases that dissociate easily in water, such as $NO_2$ or $NH_3$. The reason for this changed detection characteristic is the presence of a thin film of water on the sensitive semiconductor surface, with a thickness d ~1-10 nm. The sensor reaction which points in different directions when exposed to $NO_2$ or $NH_3$ suggests that the metal oxide sensor simply reacts to the effective pH value in the surface water.

Comparing room temperature data with high temperature data in a comparative test, it is evident that the response times at room temperature (RT) and high temperature (410° C.) are comparable and good, but that the decay time at room temperature (RT) is much worse than at 410° C. This slow decay time is the result of the electrolytic dissociation of $NO_2$ in the surface water and the subsequent hydration of the created $NO_3$ ions:

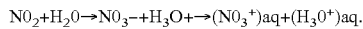

$$NO_2 + H_2O \rightarrow NO_3^- + H_3O^+ \rightarrow (NO_3^-)aq + (H_3O^+)aq.$$

The strongly increased molecular mass of the hydrated ions impedes evaporation after exposure to $NO_2$ has stopped and effective recovery of the sensor base resistance occurs only after the sensor is exposed to $NH_3$. The dissolved $NO_2$ does not evaporate in this case, but it is electrolytically neutralised. Similar gas sensitising effects can also be observed with other semiconductor materials.

The relatively low sensitivity and especially the relatively poor response and decay characteristic is a disadvantage of all the aforementioned sensor systems.

The particularly slow decay may result in accumulation and drift effects, should several short time gas exposures be superimposed, which complicate the interpretation of measured sensor signals.

The object of the invention is therefore to avoid the disadvantages of the known solutions of the prior art and to make available an improved and more cost-effective solution to the detection of trace gases.

This objective is achieved according to the invention by means of a device for the detection of trace gases with the elements of Patent Claim 1 and a corresponding method with the elements of Patent Claim 8. Preferred embodiments and further embodiments of the invention are described in the dependent claims.

The gas detection system in accordance with the invention for the detection of gases, vapours and biological pathogens is provided with at least one receptor 4, which is attached to a line connecting the ambient air with an air reservoir, wherein the gas detection system is embodied as "breathing" system containing clean, $CO_2$ bearing, moisture-saturated air in the air reservoir and whereby the working temperature of the gas detection system is room temperature. Measurement samples are acquired by sucking in a cold, dry volume of ambient air (inhaling) through the open end of the line. This air flows through the line and reaches a receptor. The current flowing through the receptor changes as relevant gases, vapours or biological pathogens attach to the receptor. The measurement results may vary depending on the type of substance and the specific receptor.

The surface of the receptor 4 is rinsed (the so-called exhaling process) after the measurement by discharging a warm, moist volume of air from the air reservoir.

This avoids the disadvantages of the known solutions of the prior art and makes available an improved and more cost-effective solution to the detection of trace gases.

In a preferred embodiment of the invention, at least one receptor is provided with a moisture film for dissolving soluble substances. This enables the measurement of substances that are soluble in fluids.

In a further preferred embodiment of the invention, the temperature of the air in the air reservoir is about 37° C. Measurements showed that this temperature is sufficient to guarantee the required measurement accuracy. Higher temperatures are possible as well, but require higher energy expenditure.

In another preferred embodiment of the invention, an array of different receptors is provided. In this way different gases, vapours and biological pathogens can be detected in parallel.

A further embodiment of the invention described above concerns the use of semiconductor substrates. Moisture films adsorbed on semiconductor substrates can exchange charge-carriers by means of this film. In this way, the surface conductivity and the space charge capacity under the semiconductor surface are modulated. Tests on metal oxides and diamond layers have shown that this can be used to measure the effective pH of the moisture film.

The substrate (IDC/interdigitated contact, semiconductors) may be coated with special binding molecular receptors to detect specific substances. In a preferred embodiment, the substrate is coated with odour-binding proteins.

In another preferred embodiment, bacteria may be detected. Specific bacteria are hereby provided as receptors 4 to combine with suitable antibodies (proteins). The created bacteria-antibody complex may then be detected by suitable means. The real-time sampling method may be applied here as well.

The method in accordance with the invention for the detection of gases, vapours and biological pathogens using the gas detection system described above comprises the following steps:
Depositing measurement samples on a receptor by sucking in a cold, dry volume of ambient air (inhaling); and
Rinsing (exhaling) the receptor 4 surface after the measurement by discharging a warm, moist volume of air from an air reservoir.

In a preferred further embodiment of the method in accordance with the invention, the surface of the receptor is rinsed (exhaling) by discharging a warm, moist volume of air from the air reservoir before depositing the measurement samples.

In another preferred embodiment of the method in accordance with the invention, the measurement is performed by real time sampling at room temperature, using a computer-based analysis unit.

Figure 2:
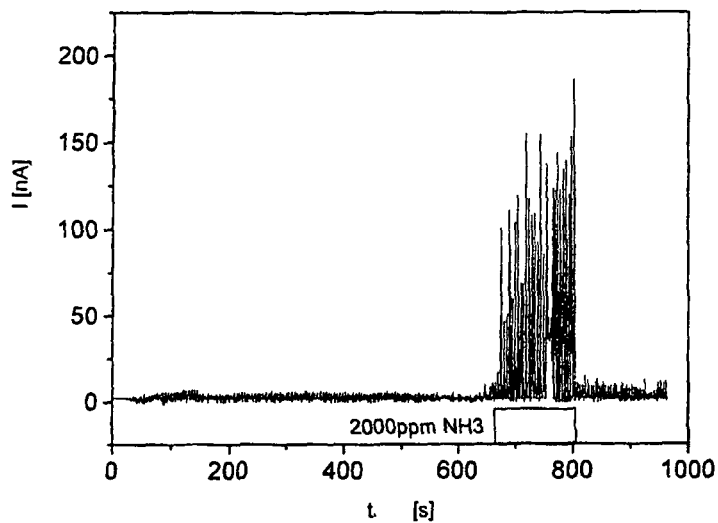
Figure 3:
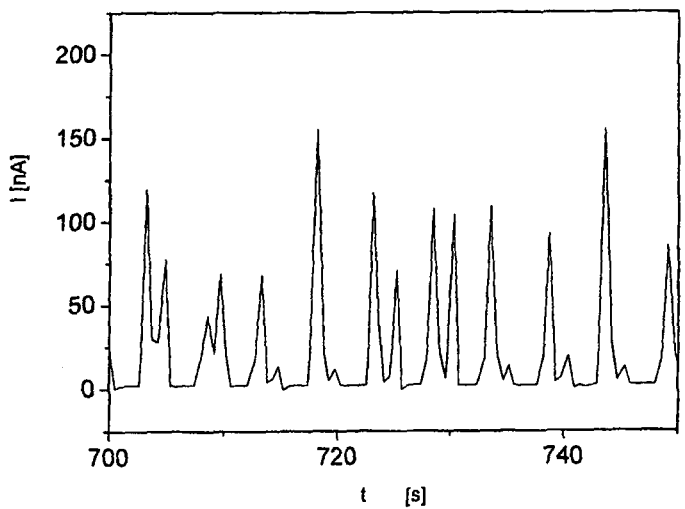
Figure 4:
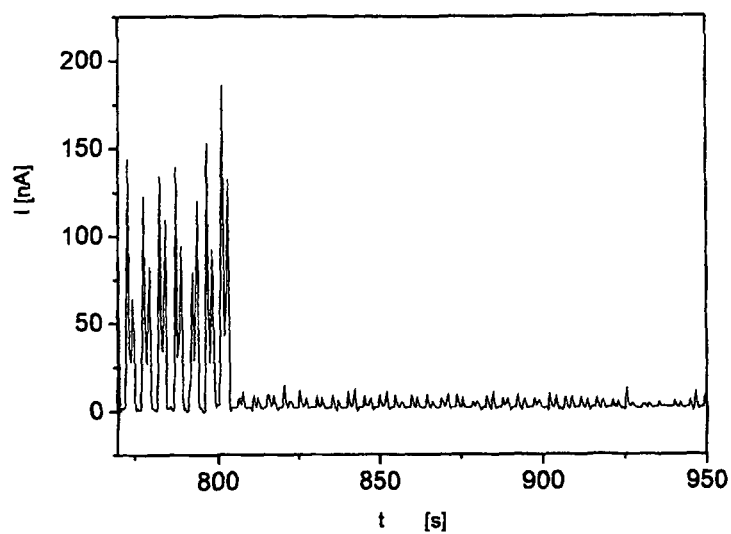

Further measures for improvement of the invention are hereinafter described in more detail, together with the description of a preferred embodiment of the invention and the figures. The figures show:
FIG. 1 a schematic functional principle of a "breathing" gas detection system in accordance with the invention;
FIG. 2 a measurement of $NH_3$ in breathing mode, using a Pt-IDC (Platinum interdigitated contact) structure;
FIG. 3 a section of FIG. 2 showing the measurement of $NH_3$ in breathing mode, using a Pt-IDC;
FIG. 4 a section of FIG. 2 showing the measurement of $NH_3$ in breathing mode, using a Pt-IDC.

The measuring method in accordance with the invention is shown schematically in FIG. 1. This shows a "breathing" gas detection system 1 with measurements using Pt-IDC receptors, i.e. the sensors are operated under continuously alternating warm, moist and cold, dry air—hereinafter called breathing mode. This is a real-time sampling method for the detection of gases, vapours and biological pathogens at room temperature (~20° C.). The breathing mode of the gas detection system 1 ensures constant cycles of cleaning the receptors 4 connected to the line 5 and analysis of the ambient air 7. Line 5 connects an air reservoir 2 to the ambient air 7. The receptors 4 are located between these. The measuring frequency is equal to one breathing cycle. When the gas detection system 1 exhales through line 5, as shown in FIG. 1a), the air reservoir 2 located at the end of the line releases clean $CO_2$ bearing air.

This volume of air is saturated with moisture and has a temperature of approx. 37° C. The arrow shows the direction of airflow in line 5. Since the gas detection system 1 works at room temperature, i.e. it is significantly colder, the moisture condenses on the surfaces of the receptors 4 in the gas detection system 1 (BET-isotherms) where it forms a clean moisture film 3 of several molecular layers. This uniquely defines the condition of the receptors 4.

During inhaling, as shown in FIG. 1b), there is both a dissociation of soluble substances in the moisture film 6 and a docking on of molecules to suitable receptors 4. Since an air volume of the order of 1 litre flows past the thin moisture film during inhaling, as shown by the arrows, successful dissociation may significantly increase the concentration of the inhaled analyte gases. Taking, for instance, a surface area of 1 $cm^2$ with a 10 nm adsorbed moisture film, then a maximum increase in concentration K of $$K = V_{air}/V_{moisture\,film} \sim 1\,000\ cm^3/10^{-6}\ cm^3 \sim 10^9$$

is possible. It should further be considered that the moisture film 6 on the surfaces of the receptors 4 will evaporate, dependant on the lower temperature and humidity of the inhaled ambient air 7. This limits the capacity of the moisture film 6 and finally forces the dissociated and hydrated analyte molecules to dock onto the specific receptors 4. Optimal detection of the most diverse pollutants is now possible.

During subsequent rinsing (exhaling), as shown in FIG. 1c), the receptors 4 are cleaned again and receive a clean new moisture film 3.

The results of an $NH_3$ measurement in breathing mode are shown in the example of FIG. 2, using simple platinum interdigitated electrodes. The diagram shows the current I (nA) against time t (s).

Warm, moist air condenses on the colder IDC in the exhaling phase. The moist condensate creates a conducting film on the surface. The current is now a few nA. In the subsequent inhaling process, dry air is sucked in over the IDC, the moisture evaporates and the conductivity plummets. Over a period covering many inhaling and exhaling cycles (t<650 s), a small, periodical and very noisy sensor signal may be observed. If an $NH_3$ concentration of 200 ppm is now added to the ambient air, then this gas will dissolve in the moisture film and by this basic dissociation increase the conductivity of the moisture film. The signal then increases in magnitude to approx. 100 times its value in clean air.

FIG. 3 shows the period of exposure to $NH_3$ in expanded view. This clearly shows the signal returning to zero again in the rinsing period (exhaling).

FIG. 4 shows another section of FIG. 2. This clearly shows the measurement signal returning to its initial value immediately after the gas exposure (800 s) has ended. There is therefore no lengthy gas desorption phase, as is the case with normal, diffusion-limited sensor operation.

Moist air was used as the medium for the carrier substance for dissociation and accumulation of the analyte gases in the measurements described above. A suitable solvent other than water may be used for the detection of substances that are not soluble in water.

The invention is not in its embodiment limited to the preferred embodiment described above. A number of variants can in fact be imagined which utilise the solution claimed in the patent, even if the embodiments are different.

The invention claimed is:

1. A gas detection system (1) for the detection of gases, vapors and biological pathogens embodied as an inhaling and exhaling system, the gas detection system comprising:
   an air reservoir (2) configured for containing clean, $CO_2$ bearing, moisture-saturated air;
   a conduit (5), configured to connect ambient air (7) with the air reservoir; and
   at least one receptor (4) arranged on the conduit,
   wherein the working temperature of the gas detection system is room temperature (approximately 20° C.), and
   wherein the at least one receptor (4) comprises a moisture film (3,6) laid down by the clean $CO_2$ bearing, moisture-saturated air exhaled from the air reservoir (2).

2. The gas detection system in accordance with claim 1, wherein the moisture film (3,6) of the at least one receptor (4) comprises a plurality of molecular layers.

3. The gas detection system in accordance with claim 1, wherein the temperature of the air in the air reservoir is approx. 37° C.

4. The gas detection system in accordance with claim 1 wherein the at least one receptor comprises an array of different receptors.

5. The gas detection system in accordance with claim 1 wherein the at least one receptor (4) comprises a detector comprising at least one Pt-IDC (Platinum Interdigitated Contact) structure, a semiconductor substrate, a metal-oxide layer and/or a diamond layer.

6. The gas detection system in accordance with claim 1 wherein the at least one receptor comprises an odor-binding protein.

7. The gas detection system in accordance with claim 1 wherein the at least one receptor comprises bacteria capable of combining with proteins.

8. A method, comprising:
- receiving a cold, dry volume of ambient air (7) at a conduit (5) of a gas detection system, the ambient air comprising measurement samples, wherein the conduit is connected to an air reservoir (2), and wherein the conduit comprises a receptor (4);
- exhaling a warm, moist volume of air from the air reservoir (2);
- depositing the measurement samples on a receptor (4), wherein the receptor (4) comprises a moisture film (3,6) laid down by the warm, moist volume of air exhaled by the air reservoir (2);
- taking a measurement of measurement samples using the receptor (4); and
- after taking the measurement, discharging the warm, moist volume of air from the air reservoir (2) to rinse a surface of the receptor (4).

9. The method in accordance with claim 8, further comprising:
- before depositing the measurement samples on the receptor, discharging a second warm, moist volume of air from the air reservoir (2).

10. The method in accordance with claim 8, wherein taking the measurement comprises taking the measurement using a computer-based analysis unit.

11. The method in accordance with claim 9, wherein the taking the measurement comprises taking the measurement using a computer-based analysis unit.

* * * * *